US009718929B2

(12) United States Patent
Gruell et al.

(10) Patent No.: US 9,718,929 B2
(45) Date of Patent: *Aug. 1, 2017

(54) CHELATING AMPHIPHILIC POLYMERS

(71) Applicant: KONINKLIJKE PHILIPS N.V., Eindhoven (NL)

(72) Inventors: Holger Gruell, Eindhoven (NL); Anke De Vries, Eindhoven (NL); Sander Langereis, Mierlo (NL); Johan Lub, Valkenswaard (NL); Erica Maria Gerarda Aussems-Custers, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/713,256

(22) Filed: May 15, 2015

(65) Prior Publication Data
US 2015/0247008 A1     Sep. 3, 2015

Related U.S. Application Data

(62) Division of application No. 13/062,742, filed as application No. PCT/IB2009/053921 on Sep. 8, 2009, now Pat. No. 9,034,298.

(30) Foreign Application Priority Data

Sep. 9, 2008  (EP) .................................... 08163933

(51) Int. Cl.
| C08G 81/02 | (2006.01) |
| A61K 9/107 | (2006.01) |
| A61K 9/51 | (2006.01) |
| A61K 49/12 | (2006.01) |
| A61K 49/18 | (2006.01) |
| A61K 51/06 | (2006.01) |
| A61K 51/12 | (2006.01) |
| A61K 9/127 | (2006.01) |
| A61K 49/04 | (2006.01) |

(52) U.S. Cl.
CPC ............ *C08G 81/025* (2013.01); *A61K 9/107* (2013.01); *A61K 9/1075* (2013.01); *A61K 9/1273* (2013.01); *A61K 9/5146* (2013.01); *A61K 49/0414* (2013.01); *A61K 49/126* (2013.01); *A61K 49/1806* (2013.01); *A61K 49/1812* (2013.01); *A61K 49/1818* (2013.01); *A61K 51/06* (2013.01); *A61K 51/065* (2013.01); *A61K 51/1217* (2013.01); *A61K 51/1237* (2013.01); *A61K 51/1251* (2013.01)

(58) Field of Classification Search
CPC ......... A61K 49/12; A61K 51/06; A61K 51/12
See application file for complete search history.

(56) References Cited

U.S. PATENT DOCUMENTS

| 5,534,499 A | 7/1996 | Ansell |
| 5,817,292 A | 10/1998 | Snow |
| 6,090,408 A | 7/2000 | Li et al. |
| 6,835,394 B1 | 12/2004 | Discher |
| 7,045,283 B2 | 5/2006 | Marks |
| 2005/0019265 A1 | 1/2005 | Hammer |
| 2005/0180922 A1 | 8/2005 | Discher |
| 2007/0253899 A1 | 11/2007 | Al |
| 2008/0166382 A1 | 7/2008 | Hsich |

FOREIGN PATENT DOCUMENTS

| EP | 1279682 A1 | 1/2003 |
| WO | 2005016259 A2 | 2/2005 |
| WO | 2007038763 A1 | 4/2007 |
| WO | 2007141761 A1 | 12/2007 |
| WO | 2008058963 A1 | 5/2008 |

OTHER PUBLICATIONS

Torchilin, Vladimir P. "Polychelating Amphiphilic Polymers (PAP) as Key Components of Microparticulate Diagnostic Agents" CHEMTECH 1999, vol. 29, No. 11, pp. 27-34.
Terreno, Enzo et al "From Spherical to Osmotically Shrunken Paramagnetic Liposomes: An Improved Generation of LIPOCEST MRI Agents with Highly Shifted Water Protons"; Angew. Chem. Int. Ed. 2007, vol. 46, pp. 966-968.
Ponce, Ana M. et al "Magnetic Resonance Imaging of Temperature-Sensitive Liposome Release: Drug Dose Painting and Antitumor Effects", Journal National Cancer Inst. 2007, vol. 99, pp. 53-63.
Vexler, Vladimir S. et al "Effect of Varying the Molecular Weight of the MR Contrast Agent Gd-DTPA-Polylysine on Blood Pharmacokinetics and Enhancement Patterns", JMRI, 1994, pp. 381-388.
Zhang, Guodong et al "Micelles Based on Biodegradable Poly(L-glutamic acid)-b-Polylactide with Paramagnetic Gd Ions Chelated to the Shell Layer as a Potential Nanoscale MR-Visible Delivery System", Biomacromolecules, vol. 9, No. 1, Jan. 2008.
Wooley, Karen et al "Strategies for Optimized/Rediolabeling of Nanoparticles for in vivo PET Imaging", Advanced Materials, 2007, vol. 19, pp. 3157-3162.
Torchilin, Vladimir P. "Lipid-Core Micelles for Targeted Drug Delievery", Current Drug Delivery, 2005, vol. 2, pp. 319-327.

*Primary Examiner* — Michael G Hartley
*Assistant Examiner* — Jagadishwar Samala

(57) ABSTRACT

Described are amphiphilic polymers that are provided with chelating moieties. The amphiphilic polymers are block copolymers comprising a hydrophilic block and a hydrophobic block, with the chelating moieties linked to the end-group of the hydrophilic block. The disclosed polymers are capable of self-assembly into structures such as micelles and polymersomes. With suitable metals present in the form of coordination complexes with the chelating moieties, the chelating amphiphilic polymers of the invention are suitable for use in various imaging techniques requiring metal labeling, such as MRI ($T_1/T_2$ weighted contrast agents or CEST contrast agents) SPECT, PET or Spectral CT.

8 Claims, 4 Drawing Sheets
(4 of 4 Drawing Sheet(s) Filed in Color)

CHELATING AMPHIPHILIC POLYMERS

CROSS REFERENCE TO PRIOR APPLICATIONS

This application is a divisional application of U.S. Ser. No. 13/062,742, filed on Mar. 8, 2011 which is the U.S. National Phase application under 35 U.S.C. §371 of International Application No. PCT/IB2009/053921, filed on Sep. 8, 2009, which claims the benefit of European Patent Application No. 08163933.8, filed on Sep. 9, 2008. These applications are hereby incorporated by reference herein.

FIELD OF THE INVENTION

The invention relates to amphiphilic polymers, and nanocarriers such as polymersomes made thereof, suitable for use as imaging contrast agents. Particularly, the invention relates to $T_1$ and/or $T_2$ contrast agents for Magnetic Resonance Imaging (MRI), to radiolabeling agents in Single Photon Emission Computed Tomography (SPECT) or Positron Emission Tomography (PET), to high Z elements in (spectral) Computed Tomography (spectral CT), and to Chemical Exchange-dependent Saturation Transfer (CEST) contrast agents for MRI. More particularly, the invention relates to image guided drug delivery based on polymersomes as drug carriers.

BACKGROUND OF THE INVENTION

A background reference on amphiphilic materials in which, e.g., a radionuclide or an MR active metal can be incorporated is e.g. V. Torchilin, Chemtech 1999, Volume 29, Number 11, 27-34. This paper refers to polychelating amphiphilic polymers. These are predominantly polymers based on poly-L-lysine comprising a hydrophilic fragment with multiple chelating groups and a relatively short, highly lipophilic phospholipid fragment. The latter serves to incorporate the polymer into liposomes and micelles.

The invention pertains to a different class of amphiphilic polymers, viz. those that are capable of self-assembly into polymersomes, micelles, or polymer-stabilized emulsions. These polymers can generally be described as block polymers comprising at least one hydrophilic block (A), preferably having a chain of more than 500 g/mole molecular weight, and at least one hydrophobic block (B), also in the form of a polymer block (i.e. not a lipid). These polymers can take the form of a block copolymer AB, of a triblock polymer ABA or BAB, or of any further block polymer having a terminal hydrophilic block and a terminal hydrophobic block, including polymers comprising a chain (C) having ambiguous solvent properties (i.e. neither hydrophilic nor hydrophobic), e.g. a block terpolymer ACB. In general, this will mean that the block C forms either a new hydrophilic block, together with block A, or a new hydrophobic block, together with Block B.

As a result of the presence of a hydrophilic and a hydrophobic block, amphiphilic polymers have the ability to form self-assembled structures. The most typical self-assembled structures are micelles and polymersomes as formed in aqueous environment. In either case, however, depending on the medium in which they are formed, either type of block (i.e. hydrophilic or hydrophobic) can form the inside or the outside. In micelles the inside comprises converging, inwardly pointing polymeric chains and the outside comprises diverging, outwardly pointing polymeric chains. In polymersomes, the self-assembled structure comprises a wall enclosing a cavity. The wall most typically, alike liposomes, is formed by a polymeric bilayer, in an aqueous medium having the hydrophobic blocks directed towards each other at the inside of the bilayer and the hydrophilic blocks at the inside of the cavity and at the outside surface of the polymersome.

As opposed to lipid vesicles (i.e. liposomes), polymersomes are chemically more stable, less leaky, less prone to interfere with biological membranes, and less dynamic due to their lower critical aggregation concentration. These properties result in less opsonisation and longer circulation times. On the other hand, liposomes offer the advantage that imaging agents or targeting moieties can easily be incorporated into the lipid layer. Liposomes can also be used very well as contrast agents, in which case they are provided e.g. with a paramagnetic label for MRI or a radionuclide for SPECT or PET.

Though liposomes offer a very versatile approach, a major limitation is the low degree of PEGylation, i.e. providing the surface with covalently attached poly (ethylene glycol). PEGylation is a known technique to mask entities, such as therapeutic proteins, when introduced into a person's body from the immune system of the person. This is believed to be based on a lower degree of opsonisation, as a result of which PEGylated surfaces are less prone to macrophage uptake. This serves to increase the circulation time of the PEGylated entity. For liposomes and other nanocarriers to be practically suitable, it is thus desired to similarly mask them, i.e. to providetealth, PEGylated nanocarriers.

SUMMARY OF THE INVENTION

It would be advantageous to provide amphiphilic polymers that are capable of forming self-assembled structures, comprising a hydrophilic block and a hydrophobic block, wherein the hydrophilic block is provided with a chelating moiety as an end-group. Particularly, it would be advantageous to provide immune-system masked (stealth) structures that can be provided with labels useful in imaging techniques.

Preferably, it would be desired to provide such materials and even better facilitate the inclusion of a label such as a metal ion or a high-Z element. paramagnetic or radio label.

In order to better address the aforementioned desires, the invention provides a chelating amphiphilic polymer that is capable of self-assembly (into a polymersome, a micelle, or a polymer-stabilized emulsion).

In one aspect, an amphiphilic polymer is provided comprising a hydrophilic block, particularly a poly (ethylene oxide) block, and a hydrophobic block, wherein the hydrophilic block is provided with a chelating moiety as an end-group.

In another aspect, a polymeric particle (also referred to as a nanocarrier) is provided comprising a self-assembled structure, such as a polymer-stabilized emulsion (i.e. an oil-in-water emulsion in which the polymer forms a layer around oil droplets), a micelle, or a bilayer enclosing a cavity (a polymersome), wherein the polymer is an amphiphilic polymer comprising a hydrophilic block and a hydrophobic block, wherein the hydrophilic block is provided with a chelating moiety as an end-group.

In yet another aspect, an MRI contrast agent is provided in the form of a nanocarrier comprising a self-assembled structure as described hereinbefore, wherein chelating moieties at the outside surface of the nanocarrier are coordinated with a paramagnetic metal.

In a further aspect, a Chemical Exchange-dependent Saturation Transfer (CEST) contrast agent for Magnetic Resonance Imaging (MRI) is presented that comprises a polymersome comprising a polymeric shell enclosing a cavity, wherein the cavity comprises a pool of proton analytes, and wherein the shell allows diffusion of the proton analytes, the shell being an amphiphilic polymer comprising a hydrophilic block and a hydrophobic block, wherein the hydrophilic block is provided with a chelating moiety as an end-group, and wherein a paramagnetic metal is coordinated with chelating moieties on the inside of the cavity.

In yet another aspect, a radiolabeling agent for use in Single Photon Emission Computed Tomography (SPECT) or in Positrone Emission Tomography (PET) is provided, in the form of a nanocarrier comprising a self-assembled structure as described hereinbefore, wherein chelating moieties at the outside surface of the nanocarrier and/or at the inside of a cavity, are coordinated with a radionuclide.

In still another aspect, an image contrast agent for (spectral) CT is provided, in the form of a nanocarrier comprising a self-assembled structure as described hereinbefore, wherein chelating moieties at the outside surface of the nanocarrier and/or at the inside of a cavity, are coordinated with a high-Z material (e.g. an element such as a heavy metal).

The invention further includes methods of making and using the chelating amphiphilic polymers, with a particular use involving drug delivery.

DETAILED DESCRIPTION OF THE INVENTION

In a broad sense, the invention can be described as a chelating amphiphilic polymer capable of self-assembly. Different from other nanocarriers, the polymer of the invention is itself capable of chelation, i.e. of forming a coordination complex with a metal ion. Different from other chelating polymers, the polymer of the invention is capable of forming a self-assembled structure (e.g. forming a polymersome rather than being attached to an otherwise existing liposome), making it suitable for use as a nanocarrier.

In a most straightforward form, the polymer can be described with reference to its three main functional elements: a hydrophobic block that has a tendency to be repelled by an aqueous environment, a hydrophilic block that has a tendency to seek contact with an aqueous environment, and a chelating moiety that is placed at the terminus of the hydrophilic block, i.e. at the remaining functional residue of the terminal monomer of the hydrophilic block. It can be envisaged that the polymer chain comprises further reactive side-groups that can also be provided with chelating moieties, but this has a drawback in that it will not normally be possible to provide a 100% side group modification, and thus the polymer will inevitably end up with reactive, usually charged side-groups. As is the case with polylysine based materials, this jeopardizes the ability of self-assembly.

The chelating moiety can be provided with a metal so as to form a coordination complex and thus provide an intrinsically 'metalized' polymer. Depending on the metal of interest, the labeled polymers can be used as contrast agents for MRI ($T_1$, $T_2$, CEST), nuclear imaging (SPECT, PET), or spectral CT.

The chelating amphiphilic polymer, when placed in aqueous environment, will be capable of forming self-assembled structures in which the hydrophilic block, and thus the chelating moiety, is directed towards the aqueous environment.

This can refer to micelles, in which the hydrophobic ends converge into a core, and the hydrophilic ends stick out three-dimensionally. In the case of micelles, a metal can be introduced to form a coordination complex with the chelating moiety either before or after formation of the micelle, as the result will be basically the same.

This can also refer, as is preferred according to the invention, to polymersomes in which the amphiphilic polymer, in aqueous environment, is made to form a bilayer enclosing a cavity. Herein which the hydrophobic blocks point towards each other at the inside boundary of the bilayer, and the hydrophilic blocks point both towards the outside aqueous environment and to the inside cavity. In this case two fundamentally different ways of forming metal coordination complexes with the amphiphilic polymer can be envisaged. One is to first allow the polymersome to be formed, and then provide the metal. In that case, at the inside cavity of the polymersome no metal bound to the polymer is present. The other is to first provide the metal, thus having substantially all chelating moieties form a coordination complex, and then form the polymersomes. In that case, the coordinated metal is present both at the inside surface of the polymersome (i.e. the inner wall of the cavity) and the outside surface of the polymersome. In the latter case, dependent on the coordination chemistry used, it will also be possible to remove the metal from the outside surface, or to substitute a different metal for the metal present at the outside surface This provides a desirable flexibility of design, e.g. allowing the polymersome to assume contrast functions in different techniques.

Whether polymersomes or micelles can be obtained is determined, in an aqueous environment such as the human body, by the hydrophilic fraction ($f_{phil}$) of the amphiphilic copolymer ($f_{phil}=M_{w,phil}/(M_{w,phil}+M_{w,phob})$). Herein $M_{w,phil}$ and $M_{w,phob}$ are the weight-average molecular weights of the hydrophilic respectively hydrophobic fractions of the polymer. In aqueous conditions, polymersomes (i.e. block copolymer vesicles) are formed for $0.2<f_{phil}<0.4$, whereas polymeric micelles are observed at $f_{phil}>0.5$. In the case of polymersomes, the amphiphilic block copolymers assemble into a head-to-tail and tail-to-head bilayer structure.

The self-assembled structure of the invention can also be a polymer-stabilized oil-in-water emulsion. In this case a monolayer of the amphiphilic polymer is formed around oil droplet, the hydrophobic part directed to the oil surface, and the hydrophilic part directed to the surrounding aqueous phase. This finds utility e.g. in CT (using an iodinated oil), F-MRI (using a perfluorinated oil), and drug delivery (several FDA approved emulsions for drug delivery exist, e.g. based on soybean oil).

Various elements of the invention are further described hereinafter.

Amphiphilic Polymer

Amphiphilic polymers capable of self-assembly are in themselves known, as are the resulting nanocarriers, such as self-assembled polymersome structures. The person skilled in the art has a suitable armamentarium to create these polymers. References include patent documents such as WO 2005/016259, U.S. Pat. No. 6,835,394, US 2005/180922, EP 1279682, US 2008/166382, WO 2008/58963, as well as various background references mentioned in these documents.

The polymer of the invention generally comprises at least one terminal hydrophilic block (A) and at least one terminal hydrophobic block (B). In a preferred, most simple form the polymer is a block copolymer having just the two aforementioned blocks, i.e. a polymer of the general structure AB. These blocks themselves preferably consist essentially of a single repeating monomeric unit ($M_A$ respectively $M_B$). The resulting block copolymer structure thus satisfies the general structural formula (i).

$$X\text{-}[M_A]_n\text{-}[M_B]_m \quad (i)$$

wherein X represents a chelating moiety; $M_A$ represents a hydrophilic repeating unit; $M_B$ represents a hydrophobic repeating unit; n and m each independently are integers representing the number of monomeric units forming the block. As to the number of repeating units, this should be sufficient to extend an amphiphilic character to the polymer and will generally be at least 3. The maximum is not particularly critical, and is given by regular considerations related to polymer production technology. A typical upper limit is thus 1,000,000. A preferred range for n and m is of from 4 to 40.000, preferably of from 5 to 5,000, and most preferably of from 10 to 225.

It is possible, however, that either or both of the hydrophilic and hydrophobic blocks comprise two or more different repeating units, thus providing a polymer that satisfies the general formula (ii):

$$[M_{A1}]_p\text{-}[M_{A2}]_q\text{-}[M_{A3}]_r\text{-}[M_{B1}]_x\text{-}[M_{B2}]_y\text{-}[M_{B2}]_z \quad (ii)$$

Herein $M_{A1}$, $M_{A2}$, and $M_{A3}$ denote different hydrophilic repeating units, and $M_{B1}$, $M_{B2}$, and $M_{B3}$ denote different hydrophobic repeating units. The letters p, q, r, x, y, and z each independently represent integers of from 0 to 1,000,000 with the proviso that (p+q+r) and (x+y+z) range of from 3 to 1,000,000, preferably of from 4 to 40,000 more preferably of from 5 to 5,000, and most preferably of from 10 to 225. Analogous multiblock polymers, met a larger number of different repeating hydrophilic and hydrophobic units are possible, though not preferred.

It is also possible, in the polymers of either of the foregoing formulae (1) and (2), that a block (C) of ambiguous solvent behavior is incorporated, i.e. a block that is neither hydrophilic nor hydrophobic. The hydrophilic block or blocks generally are blocks that are soluble in water, and preferably are selected from the group consisting of poly (ethylene oxide), poly (meth)acrylic acid, derivatives of polyacrylamide, poly alcohols such as poly (vinyl alcohol) or poly (hydroxy ethyl methacrylate), hydrophilic polypeptides, and sugar derivatives. Most preferably, the hydrophilic block is a poly (ethylene oxide) block (PEO, PEG), since therewith the polymer of the invention is intrinsically "PEGylated." in the aqueous environment of the human or animal body, the hydrophilic poly (ethylene oxide), i.e. PEG, block will form the outside surface of the self-assembled structure (such as a polymersome) formed, thus providing a 100% PEGylated surface, hence optimal stealth (leading to longer circulation times as a result of less opsonisation). With reference to the aforementioned factor $f_{phil}$, it is preferred that the weight-average molecular weight of the poly (ethylene oxide) block is of from 500 to 10.000. Longer hydrophilic blocks would result in a need for relatively long hydrophobic blocks, which is less desired in view of the lower biodegradability and the more difficult processing (high viscosity), The hydrophobic block or blocks generally lack an affinity for water, and preferably are selected from polymers having a Tg below 70° C. such as poly (butadiene), poly (isoprene), poly (ethylethylene. In general, all polymers having a backbone of carbon atoms and side groups of hydrophobic nature, can be used for the hydrophobic block.

The aforementioned Tg preference too relates int.al. to processing, as polymers having a Tg above this Tg value are more difficult to process in view of their high viscosity, and/or in view of their crystallinity under processing conditions. In the case of such high Tg polymers it will be preferred to employ plasticizers during processing (e.g. organic solvents such as THF (tetra hydro furan) or dichloro methylene. These plasticizers serve as a processing tool, and are removed before using the polymer. This processing technology is regularly available to the person skilled in the art of polymer science.

As the skilled person will understand, a great degree of design flexibility is given by standard methods to influence the molecular weight, and the molecular weight distribution, of the amphiphilic polymers. This can also be viewed from the angle of the number of end-groups per unit of polymer weight, which thus provides a simple tool to tailor the number of chelating groups per unit of polymer weight. A particular advantage can be obtained by combining a chelating amphiphilic polymer with a relatively short hydrophilic chain (notably a PEG chain) with an amphiphilic polymer having a relatively large PEG chain. In a resulting self-assembly, the chelating moiety will thus be contained within the polymer layer forming the self-assembled structure, whilst PEG chains will form the outer surface of the structure, thus providing a full PEG surface undisturbed by chelating moieties.

Chelating Moiety

The chelating moiety can be derived and/or selected from moieties, which contain electron donor atoms. These moieties can be selected from, for example, polyphosphates, such as sodium tripolyphosphate and hexametaphosphoric acid; aminocarboxylic acids, such as ethylenediaminetetraacetic acid, N-(2-hydroxyethyl)ethylenediaminetriacetic acid, nitrilotriacetic acid, N,N-di(2-hydroxyethyl)glycine, ethylenebis(hydroxyphenylglycine) and diethylenetriamine pentaacetic acid; 1,3-diketones, such as acetylacetone, trifluoroacetylacetone, and thienoyltrifluoroacetone; and hydroxycarboxylic acids, such as tartaric acid, mucic acid, citric acid, gluconic acid, and 5-sulfosalicylic acid; polyamines, such as ethylenediamine, diethylenetriamine, triethylenetetramine, and triaminotriethylamine; aminoalcohols, such as triethanolamine and N-(2-hydroxyethyl)ethylenediamine; aromatic heterocyclic bases, such as 2,2'-dipyridyl, 2,2'-diimidazole, dipicoline amine and 1,10-phenanthroline; phenols, such as salicylaldehyde, disulfopyrocatechol, and chromotropic acid; aminophenols, such as 8-hydroxyquinoline and oxinesulfonic acid; oximes, such as dimethylglyoxime and salicylaldoxime; peptides containing proximal chelating functionality such as polycysteine, polyhistidine, polyaspartic acid, polyglutamic acid, or combinations of such amino acids, each polyamino acid containing from 2 to about 20 amino acids in the polymer; Schiff bases, such as disalicylaldehyde 1,2-propylenediimine; tetrapyrroles, such as tetraphenylporphin and phthalocyanine; sulfur compounds, such as toluenedithiol, meso-2,3-dimercaptosuccinic acid, dimercaptopropanol, thioglycolic acid, potassium ethyl xanthate, sodium diethyldithiocarbamate, dithizone, diethyl dithiophosphoric acid, and thiourea; synthetic macrocyclic compounds, such as dibenzo[18]crown-6, (CH3)6-[14]-4,11-diene-N4, and (2.2.2)-cryptate; and phosphonic acids, such as nitrilotrimethylenephosphonic acid, ethylenediaminetetra(methylenephosphonic acid), and hydroxyethylidenediphosphonic acid, or combinations of two or more of the above agents.

Preferred chelating moieties contain one or more carboxylic acid or carboxylate groups and include elements present in: ethylenediamine-N,N,N',N'-tetraacetic acid (EDTA); N,N,N',N'',N''-diethylenetriaminepentaacetic acid (DTPA); 1,4,7,10-tetraazacyclododecane-N,N',N'',N'''-tetraacetic acid (DOTA); 1,4,7,10-tetraazacyclododecane-N,N',N''-triacetic acid (DO3A); 1-oxa-4,7,10-triazacyclododecane-N,N',N''-triacetic acid (OTTA); trans(1,2)-cyclohexanodiethylenetriamine pentaacetic acid (CDTPA).

The most preferred chelating moieties are DOTA, DTPA, HYNIC (6-hydrazinonicotine used for the chelation of technetium), and desferoxamine (e.g. available as desforaxmine mesylate under the proprietary name of Desferal) used for the chelation of gallium.

It will be understood by the skilled person, that the foregoing examples are chelating compounds, and that the chelating moiety, as compared to these compounds, are in fact derivatives thereof in the sense that they include a linkage to the polymer.

Coupling of the Chelating Moiety

Although other orders of processing are not excluded, it is preferred to first make the amphiphilic copolymer and then couple the chelating moiety to the hydrophilic block thereof. As the person skilled in the art will understand, the exact linkage between the hydrophilic terminal monomer and the chelating moiety will be determined by the functional groups available on the monomer terminus and on the chelating compound that serves to form the chelating moiety in the polymer. A typical, frequently suitable linkage is an amide bond.

Preferred block poly (butadiene)-poly (ethylene oxide) polymers of the invention can be made as follows, as depicted in Scheme 1 below. First a block polymer, in this case poly (ethylene oxide)-block-poly (butadiene) (1), is provided. The primary alcohol of the polymer is converted into the corresponding tosylate of the copolymer (2). Subsequently, the tosylate is reacted with $NH_3$ to yield the amine-functionalized poly (ethylene oxide)-block-poly (butadiene) (3). Then, the amine group of 3 is reacted with the N-succimidyl ester of DOTA (4) to obtain DOTA-functionalized poly (ethylene oxide)-block-poly (butadiene) (5).

Scheme 1.

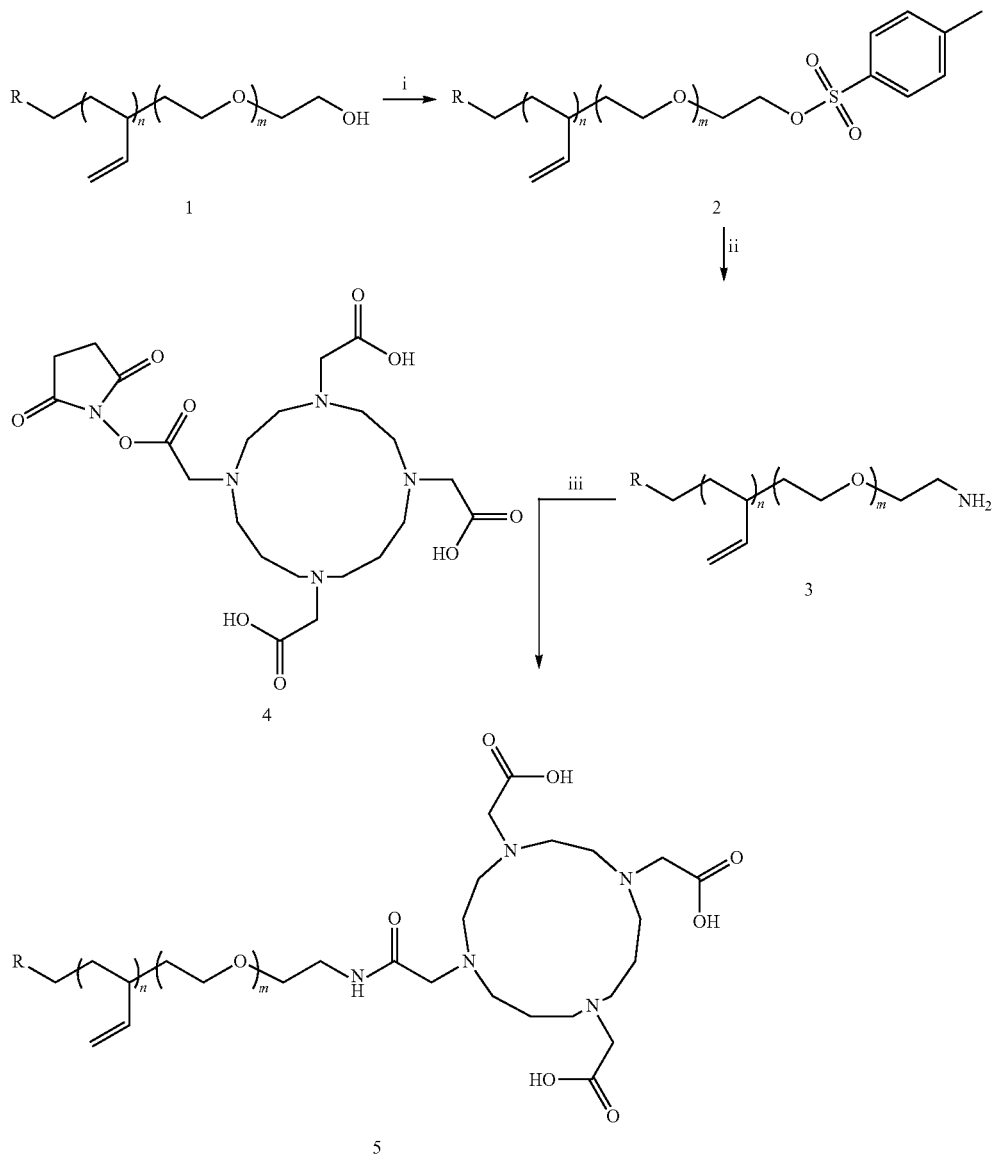

Herein the reactants and solvents are indicated as follows: (i) pTsCl, KOH, DCM; (ii) 7 N NH$_3$, toluene/MeOH; (iii) Et$_3$N, DMF.

Depending on the application of interest, the DOTA-functionalized block copolymer (5) can be mixed with non-functionalized block copolymers in ratios between a minimum of a single chelating polymer in the system to a maximum of 100% (i.e. all polymer molecules present are chelating polymers. The developed synthetic procedure can be applied to a wide range of copolymers with different molecular weights and various $f_{phil}$ values, which allows for the preparation of a wide range of self-assembled structures. Moreover, a similar synthetic strategy can be applied for the chemical modification of block copolymers with other metal coordinating ligands, such as DTPA, and targeting ligands, such as antibodies, peptides, etc.

Coordination Complexes Based on the Chelating Moiety

The chelating moieties present in the amphiphilic polymers of the invention can be employed to form coordination complexes with metals in accordance with chelating methods known in the art.

Since the amphiphilic polymers of the invention are intrinsically provided with coordination sites, a great freedom of choice exists as to the degree of chelation, which can range from a single chelated ion to the maximum obtainable (with the possibility to achieve a much higher degree of chelation than in the case of conventional, not themselves chelating, polymers).

With the example of a DOTA-based copolymer as described above, in one approach this polymer is self-assembled into polymersomes followed by Gd(III) complexation. In a second approach, the reaction with Gd(III) and the DOTA copolymer is performed in the first step and, subsequently, the Gd(III)DOTA-functionalized copolymers are self-assembled into polymersomes. In the first approach, Gd(III) is only present at the outer shell of the polymersome, i.e. the Gd(III) complexes point outward to the bulk water, whereas in the second approach the Gd(III) complexes points outside at both sides of the polymersome layer.

T$_1$/T$_2$ MRI Contrast Agent

The polymers of the invention can be used as MRI contrast agents. This generally refers to T$_1$ and/or T$_2$ weighted contrast agents.

In magnetic resonance imaging of the body of a mammal such as a human, an in vivo image of an organ or tissue is obtained by placing at least the portion of the body to be imaged in a strong external magnetic field, pulsing with radio frequency energy, and observing the effect of the pulses on the magnetic properties of the protons contained in and surrounding the organ or tissue. This is especially useful in imaging the circulatory vasculation of the body (i.e. the blood pool). A number of magnetic parameters can be measured. The proton relaxation times, T$_1$ and T$_2$, are of primary importance. T$_1$, also called the spin-lattice or longitudinal relaxation time, and T$_2$, also called the spin-spin or transverse relaxation time, are functions of the chemical and physical environment of the organ or tissue water and are measured using Rf pulsing techniques. This information is analyzed as a function of spatial location by computer, which transforms the information to generate an image.

Often the image produced lacks appropriate contrast, e.g., between normal and diseased tissue, reducing diagnostic effectiveness. To overcome this drawback, contrast agents have been used. MR contrast agents are magnetically active substances, which exert an effect on the magnetic resonance parameters of nuclei in molecules proximal to them. Theoretically, a contrast agent, if taken up preferentially by a certain portion of an organ or a certain type of tissue, e.g., diseased tissue, can provide a change in contrast or enhancement in the resultant images of that tissue.

Inasmuch as magnetic resonance images are strongly affected by variations in the T$_1$ and T$_2$ parameters, it is desirable to have a contrast agent, which affects either or both parameters. Research has focused predominantly on two classes of magnetically active materials, i.e., paramagnetic materials, which act to decrease T$_1$, and T$_2$, and super paramagnetic materials, which act primarily to decrease T$_2$. At low concentrations, paramagnetic materials affect T$_1$ more than T$_2$.

Paramagnetism occurs in materials that contain electrons with unpaired spins. Paramagnetic materials are characterized by a weak magnetic susceptibility (response to an applied magnetic field). Paramagnetic materials become weakly magnetic in the presence of a magnetic field and rapidly lose such activity, i.e., demagnetize, once the external field has been removed. It has long been recognized that the addition of paramagnetic materials to water causes a decrease in the T$_1$ parameter of the hydrogen nuclei.

Paramagnetic materials, for example, comprising the paramagnetic lanthanides, especially materials containing Gd$^{+3}$ are preferred as MRI contrast agents primarily because of their effect on T$_1$.

By virtue of the presence of a chelating moiety in the amphiphilic polymers of the invention, a paramagnetic material can be simply included in the polymer by allowing it to form a coordination complex with the chelating moiety.

It is preferred in the case of T$_1$/T$_2$ contrast agents if these are based on a self-assembled structure having the paramagnetic material present on the outside. In this case micelles are thus suitable. It is preferred, however, that the nanocarrier of the invention is in the form of a polymersome.

SPECT and PET Contrast Agent

In a similar manner as with the formation of coordination complexes of paramagnetic agents, the polymers of the invention can also be used to include radionuclides.

Single photon emission computed tomography (SPECT) generates images depicting the distribution of gamma-ray emitting nuclides. This imaging modality has a very high sensitivity and the absence of background signal allows the quantitative information on the biodistribution of the radionuclide. SPECT is commonly applied in the hospital for the visualization and quantification of tumor regions and, more recently, for the evaluation of the biodistribution of potential new drugs or contrast agents. A recent development is the synthesis of lipid-stabilized emulsions for SPECT using $^{111}$In as a radionuclide. The incorporation of DTPA- or DOTA-functionalized copolymers in polymersomes, polymeric micelles, and copolymer-stabilized emulsions allows for efficient radiolabeling of the self-assembled particle with radioactive isotopes (such as $^{177}$Lu or $^{111}$In) for nuclear imaging applications.

The invention includes the preparation and the radiolabeling of a polymer-stabilized emulsion using an amphiphilic polymer as described hereinbefore, for instance a DOTA-functionalized poly (ethylene oxide)-block-poly (butadiene), as the emulsifier.

As a proof of concept, emulsions were stabilized with our DOTA-terminated copolymer and these structures were radiolabeled with $^{111}$In. The biodistribution of the agents was studied in mice. In FIG. 7, the SPECT/CT image shows the presence of $^{111}$In in the heart, liver and kidneys. The presence of $^{111}$In in the blood 4 hours post-injection indicates a long blood circulation time of the radiolabeled emulsions. Moreover, liver accumulation indicates excretion of the nanoparticles via the hepatobiliary pathway, which is further confirmed by the absence of [111]Indium in the bladder. These results demonstrate that radiolabeled emulsions using our DOTA copolymer can be applied as SPECT agents.

Similarly, the invention finds use in PET, by providing chelation of radionuclides typically used therein such as Rubidium-82, Gallium-68, Copper-64, and Zirconium-89.

CEST MRI Contrast Agent

The polymers of the invention, self-assembled into polymersomes, are a suitable basis to form a CEST MRI contrast agent. The CEST method serves to generate image contrast by utilizing Chemical Exchange-dependent Saturation Transfer (CEST) from selected, magnetically pre-saturated protons to the bulk water molecules determined by MRI CEST in combination with a paramagnetic chemical shift reagent (ParaCEST) is a method, in which the magnetization of a pool of paramagnetically shifted protons of a CEST contrast agent is selectively saturated by the application of radio frequency (RF) radiation. The transfer of this saturation to bulk water molecules by proton exchange leads to a reduced amount of excitable water protons in the environment of the CEST contrast agent. Thus a decrease of the bulk water signal intensity is observed, which can be used to create a (negative) contrast enhancement in MRI images.

An approach to obtain a high CEST efficiency is based on utilizing the large number of water molecules of a solution containing a paramagnetic shift reagent (e.g. Na[Tm (dotma) ($H_2O$)]), wherein "$H_4$dotma" stands for $\alpha,\alpha',\alpha,''\alpha'''$-tetramethyl-1,4,7,19-tetraacetic acid and dotma represents the respective fourfold deprotonated tetra anionic form of the ligand, to provide a pool of protons that are chemically shifted and that, therefore, can selectively be saturated by an RF pulse. If this system is encapsulated in a carrier, here a polymersome, the magnetic saturation can be transferred to the bulk water molecules, at the outside of the carriers, which are not chemically shifted. The amount of magnetization transfer and hence the extent of contrast enhancement are determined by the rate of the diffusion of water through the shell of the carrier (i.e. the water exchange rate), as well as by the amount of water within the carrier.

The optimum water exchange rate is directly correlated with the chemical shift difference between the proton pool inside of the carrier and the bulk water outside of the carrier. The paramagnetic shift that is induced on the water molecules inside the polymersomes consists of two main contributions: chemical shift resulting from a direct dipolar interaction between the water molecules and the shift reagent ($\delta_{dip}$), and chemical shift caused by a bulk magnetic susceptibility effect ($d_{bms}$). The overall paramagnetic shift is the sum of these two contributions:

$$\delta = \delta_{dip} + \delta_{bms} \quad (1)$$

$\delta_{bms}$ is zero for spherical particles, but it can be significant for anisotropic particles. The aspherical particles experience a force in a magnetic field, which causes them to align with the magnetic field lines. In the case of liposomes it has been demonstrated that the overall paramagnetic shift can be further increased, if they bear paramagnetic molecules associated with the phospholipid membrane.

A reference on CEST using aspherical liposomes is Terreno, E. et al. Angew. Chem. Int. Ed. 46, 966-968 (2007).

By virtue of the presence of a chelating moiety in the amphiphilic polymers of the invention, a paramagnetic material can be simply included in the polymer by allowing it to form a coordination complex with the chelating moiety. This enables the incorporation of a suitable paramagnetic material (preferably a lanthanide and most preferably Tm or Dy) in any ratio in the polymer.

Similarly to the method described above for MRI ($T_1/T_2$) contrast agents, the lanthanide can be provided at the outside surface or also at the inside surface of the polymersome. It should be noted that, in respect of CEST, the invention provides a good deal of design freedom. The polymersome can be used as a more or less standard CEST contrast agent, by providing the pool of protons inside the cavity with a dissolved or suspended suitable paramagnetic material, such as a lanthanide. The chelating outside of the polymersome can be used to form a coordination complex with a further paramagnetic metal, by virtue of which the chemical shift difference to the saturation transfer protons in the environment of the polymersomes, can be further enhanced (thus enhancing the aforementioned bulk susceptibility effect). Additionally, the paramagnetic material inside the cavity can be provided in the form of a coordination complex with the chelating moieties in the polymer of the invention.

Further, in either of the foregoing embodiments, the shape of the polymersomes can be rendered aspherical, so as to enhance the CEST effect. Polymersomes will generally be spherical. Rendering the polymersomes aspherical is done by subjecting them to a dialysis process against a hypertonic buffer solution, hence a buffer solution with a higher osmolarity compared to the solution at the inside of the polymersomes. The dialysis causes a net diffusion of water from the inside of the polymersomes to the bulk solution. This reduces the total inner volume of the polymersomes. Since the surface area of the polymersomes remains constant, the volume reduction forces the polymersomes to deform and to assume an aspherical shape, such as a disk shape, a cigar shape, or any other aspherical shape.

It should be noted that, in the case of aspherical polymersomes, the CEST effect can also be obtained fully on the basis of the effect of the non-spherical shape, i.e. without a paramagnetic shift reagent substantially interacting with the MR analyte present in the cavity, or with MR analytes chosen that happen to lack interaction with the paramagnetic shift reagent present inside the cavity. In the present invention this adds to the flexibility of design: as noted above, the cavity can be selected not to be loaded with a metal. In this case the polymersome, if rendered aspherical, can be used as CEST contrast agent nonetheless, and the chelation of metal at the outside surface can be used to introduce an additional contrast, e.g. based on $T_1$ and/or $T_2$.

The CEST effect can further be tuned by the nature of the blocks of the copolymer and/or the thickness of the polymer layer, since these parameters influence the rate of water exchange across the membrane; e.g. the amphiphilic nature of the polymer can be employed to affect the proton exchange rate through the polymersome. This can generally be done by changing the ratio of lengths of the more hydrophilic and the more hydrophobic blocks.

As to exchange of water, it will be understood that the CEST effect can also be obtained in the case of other MR analytes, such as small organic molecules, as long as these are capable of exchange through the polymersome bilayer membrane.

Drug Delivery

Many diseases that are mostly localized in a certain tissue are treated with systemically administered drugs. A well-known example of standard cancer therapy is a systemic chemotherapy coming along with significant side effects for the patient due to undesired biodistribution and toxicity. The therapeutic window of these drugs is usually defined by the minimal required therapeutic concentration in the diseased tissue on the one hand, and the toxic effects in non-targeted organs, e.g. liver, spleen, on the other. Localized treatment by, for example, local release of cytostatics from nanocarriers promises a more efficient treatment and a larger therapeutic window compared to standard therapeutics. Localized drug delivery is also important if other therapeutic options such as surgery are too risky as is often the case for liver cancers. Localized drug delivery can also become the preferred treatment option for many indications in cardiovascular disease (CVD), such as atherosclerosis in the coronary arteries.

Magnetic Resonance Imaging is an important diagnostic technique that is commonly used in hospitals for the diagnosis of disease. MRI allows for the non-invasive imaging of soft tissue with a superb spatial resolution.

As a useful extension of its diagnostic use, MRI is also proposed for the monitoring of the delivery of bio-active agents such as therapeutic or diagnostic agents. I.e., MRI can not only be used for treatment planning, but also to control local drug delivery under image guidance. A reference in this respect is Ponce et al., J Natl Cancer Inst 2007; 99: 53-63. Herein a drug, doxorubicin, is taken up in a temperature-sensitive liposome that is solid at normal body temperature, and melts at a few degrees higher (41-42° C.). Thus, drug release can be facilitated by applying heat, as this will result in the opening-up of the liposome, whereupon drug release is no longer determined by diffusion (if any) through the liposomal shell. In order to monitor drug release by MRI, a manganese salt is added to the formulation as an MRI contrast agent.

The polymersomes of the invention can be used as a drug carrier. The administration and delivery of a drug introduced into a body via this carrier can be monitored by $T_1/T_2$ and or CEST MRI depending (as will be clear from the invention as described above) on the type and position of paramagnetic metal complexed with the amphiphilic, chelating polymer.

The drug carrier is to be introduced into the body of a person to be subjected to MRI. This will be e.g. by injection in the blood stream, or by other methods to introduce the carrier into body fluid.

A drug is a chemical substance used in the treatment, cure, prevention, or diagnosis of a disease or disorder, or used to otherwise enhance physical or mental well-being. The guided delivery foreseen with the present invention will mostly be useful for therapeutic agents (i.e. drugs in a strict sense, intended for therapy or prevention of diseases or disorders), but also for agents that are administered for diagnostic purposes. Although other bio-active agents, i.e. those that are not therapeutic or diagnostic, such as functional food ingredients, will not generally be subjected to guided and/or monitored delivery, such could be done using the present invention if desired.

The most optimal use of the invention is attained in the case of targeted therapeutics, i.e. drugs that are intended for targeted delivery, as such delivery will by nature benefit most from the monitoring made available by the invention. This pertains, e.g., to agents in the treatment of tumors to be delivered on site, to agents in the treatment or prevention of cardiovascular disorders, such as atherosclerosis in the coronary arteries, or to antithrombotic agents (e.g. for locally resolving blood cloths) or agents that require passing the blood-brain barrier such as neuromodulators as can be used in the treatment of neural conditions such as epilepsy, Alzheimer's disease, Parkinson's disease, or stroke. Benefits from the guidance and monitoring of targeted drug delivery are also applicable to targeted diagnostic agents. Similarly as with targeted therapeutics, here too cancer is an area where site-specific delivery can be of importance.

Bio-active agents suitable for use in the present invention include biologically active agents including therapeutic drugs, endogenous molecules, and pharmacologically active agents, including antibodies; nutritional molecules; diagnostic agents; and additional contrast agents for imaging. As used herein, an active agent includes pharmacologically acceptable salts of active agents.

The polymersome-based drug carriers of the present invention can comprise either hydrophilic or hydrophobic bioactive agents. A hydrophilic bioactive agent could be encapsulated in the aqueous compartment of the carrier or it could be associated with the more hydrophilic part of the particle shell or its distribution could involve a combination of these options, whereas hydrophobic bioactive agents could be incorporated in hydrophobic domains of the carrier, for instance in the polymersome shell. Nucleic acids, carbohydrates and, in general, proteins and peptides are water soluble or hydrophilic. For instance, bioactive agents which are small molecules, lipids, lipopolysaccharides, polynucleotides and antisense nucleotides (gene therapy agents) are also envisaged. Such biologically active agents, which may be incorporated, thus include non-peptide, non-protein drugs. It is possible within the scope of the present invention to incorporate drugs of a polymeric nature, but also to incorporate drugs of a relatively small molecular weight of less than 1500 g/mol, or even less than 500 g/mol.

Accordingly, compounds envisaged for use as bioactive agents in the context of the present invention include any compound with therapeutic or prophylactic effects. It can be a compound that affects or participates in tissue growth, cell growth, cell differentiation, a compound that is able to invoke a biological action such as an immune response, or a compound that can play any other role in one or more biological processes. A non-limiting list of examples includes antimicrobial agents (including antibacterial, antiviral agents and anti-fungal agents), anti-viral agents, anti-tumor agents, thrombin inhibitors, antithrombogenic agents, thrombolytic agents, fibrinolytic agents, vasospasm inhibitors, calcium channel blockers, vasodilators, antihypertensive agents, antimicrobial agents, antibiotics, inhibitors of surface glycoprotein receptors, antiplatelet agents, antimitotics, microtubule inhibitors, anti secretory agents, actin inhibitors, remodeling inhibitors, anti metabolites, antiproliferatives (including antiangiogenesis agents), anticancer chemotherapeutic agents, anti-inflammatory steroid or non-steroidal anti-inflammatory agents, immunosuppressive agents, growth hormone antagonists, growth factors, dopamine agonists, radiotherapeutic agents, extracellular matrix components, ACE inhibitors, free radical scavengers, chelators, antioxidants, anti polymerases, and photodynamic therapy agents.

Relatively small peptides may be referred to by the number of amino acids (e.g. di-, tri-, tetrapeptides). A peptide with a relatively small number of amide bonds may also be called an oligopeptide (up to 50 amino acids), whereas a peptide with a relatively high number (more than 50 amino acids) may be called a polypeptide or protein. In addition to being a polymer of amino acid residues, certain proteins may further be characterized by the so called quaternary structure, a conglomerate of a number of polypeptides that are not necessarily chemically linked by amide bonds but are bonded by forces generally known to the skilled professional, such as electrostatic forces and Vanderwaals forces. The term peptides, proteins or mixtures thereof as used herein is to include all above mentioned possibilities.

Usually, the protein and/or peptide are selected on the basis of its biological activity. Depending on the type of polymer chosen, the product obtainable by the present process is highly suitable for controlled release of proteins and peptides. In a particular embodiment, the protein or peptide is a growth factor.

Other examples of peptides or proteins or entities comprising peptides or proteins which may advantageously be contained in the loaded polymer include, but are not limited to, immunogenic peptides or immunogenic proteins, which include, but are not limited to, the following:

Toxins such as diphtheria toxin and tetanus toxin.

Viral surface antigens or parts of viruses such as adenoviruses, Epstein-Barr Virus, Hepatitis A Virus, Hepatitis B Virus, Herpes viruses, HIV-1, HIV-2, HTLV-III, Influenza viruses, Japanese encephalitis virus, Measles virus, Papilloma viruses, Paramyxoviruses, Polio Virus, Rabies, Virus, Rubella Virus, Vaccinia (Smallpox) viruses and Yellow Fever Virus.

Bacterial surface antigens or parts of bacteria such as *Bordetella pertussis, Helicobacter pylori, Clostridium tetani, Corynebacterium diphtheria, Escherichia coli, Haemophilus influenza, Klebsiella* species, *Legionella pneumophila, Mycobacterium bovis, Mycobacterium leprae, Mycrobacterium tuberculosis, Neisseria gonorrhoeae, Neisseria meningitidis, Proteus* species, *Pseudomonas aeruginosa, Salmonella* species, *Shigella* species, *Staphylococcus aureus, Streptococcus pyogenes, Vibrio cholera* and *Yersinia pestis*.

Surface antigens of parasites causing disease or portions of parasites such as *Plasmodium vivax* (malaria), *Plasmodium falciparum* (malaria), *Plasmodium ovale* (malaria), *Plasmodium malariae* (malaria), *Leishmania tropica* (leishmaniasis), *Leishmania donovani*), leishmaniasis), *Leishmania branziliensis* (leishmaniasis), *Trypanosoma rhodescense* (sleeping sickness), *Trypanosoma gambiense* (sleeping sickness), *Trypanosoma cruzi* (Chagas' disease), *Schistosoma mansoni* (schistosomiasis), *Schistosomoma haematobium* (schistomiasis), *Schistosoma japonicum* (shichtomiasis), *Trichinella spiralis* (trichinosis), Stronglyloides *duodenale* (hookworm), *Ancyclostoma duodenale* (hookworm), *Necator americanus* (hookworm), *Wucheria bancrofti* (filariasis), *Brugia malaya* (filariasis), *Loa* (filariasis), *Dipetalonema perstaris* (filariasis), *Dracuncula medinensis* (filariasis), and *Onchocerca volvulus* (filariasis).

Immunoglobulins such as IgG, IgA, IgM, Antirabies immunoglobulin, and Antivaccinia immunoglobulin.

Antitoxin such as Botulinum antitoxin, diphtheria antitoxin, gas gangrene antitoxin, tetanus antitoxin.

Antigens which elicit an immune response against foot and mouth disease.

Hormones and growth factors such as follicle stimulating hormone, prolactin, angiogenin, epidermal growth factor, calcitonin, erythropoietin, thyrotropic releasing hormone, insulin, growth hormones, insulin-like growth factors 1 and 2, skeletal growth factor, human chorionic gonadotropin, luteinizing hormone, nerve growth factor, adrenocorticotropic hormone (ACTH), luteinizing hormone releasing hormone (LHRH), parathyroid hormone (PTH), thyrotropin releasing hormone (TRH), vasopressin, cholecystokinin, and corticotropin releasing hormone; cytokines, such as interferons, interleukins, colony stimulating factors, and tumor necrosis factors: fibrinolytic enzymes, such as urokinase, kidney plasminogen activator; and clotting factors, such as Protein C, Factor VIII, Factor IX, Factor VII and Antithrombin III.

Examples of other proteins or peptides are albumin, atrial natriuretic factor, renin, superoxide dismutase, alpha 1-antitrypsin, lung surfactant proteins, bacitracin, bestatin, cydosporine, delta sleep-inducing peptide (DSIP), endorphins, glucagon, gramicidin, melanocyte inhibiting factors, neurotensin, oxytocin, somostatin, terprotide, serum thymide factor, thymosin, DDAVP, dermorphin, Met-enkephalin, peptidoglycan, satietin, thymopentin, fibrin degradation product, des-enkephalin-alpha-endorphin, gonadotropin releasing hormone, leuprolide, alpha-MSH and metkephamid.

Anti-tumor agents such as altretamin, fluorouracil, amsacrin, hydroxycarbamide, asparaginase, ifosfamid, bleomycin, lomustin, busulfan, melphalan, chlorambucil, mercaptopurin, chlormethin, methotrexate, cisplatin, mitomycin, cyclophosphamide, procarbazin, cytarabin, teniposid, dacarbazin, thiotepa, dactinomycin, tioguanin, daunorubicin, treosulphan, doxorubicin, tiophosphamide, estramucin, vinblastine, etoglucide, vincristine, etoposid, vindesin and paclitaxel.

Antimicrobial agents comprising:

Antibiotics such as ampicillin, nafcillin, amoxicillin, oxacillin, azlocillin, penicillin G, carbenicillin, penicillin V, dicloxacillin, phenethicillin, floxacillin, piperacillin, mecillinam, sulbenicillin, methicillin, ticarcillin, mezlocillin, Cephalosporins: cefaclor, cephalothin, cefadroxil, cephapirin, cefamandole, cephradine, cefatrizine, cefsulodine, cefazolin, ceftazidim, ceforanide, ceftriaxon, cefoxitin, cefuroxime, cephacetrile, latamoxef, and cephalexin. Aminoglycosides such as amikacin, neomycin, dibekacyn, kanamycin, gentamycin, netilmycin, tobramycin. Macrolides such as amphotericin B, novobiocin, bacitracin, nystatin, clindamycin, polymyxins, colistin, rovamycin, erythromycin, spectinomycin, lincomycin, vancomycin Tetracyclines such as chlortetracycline, oxytetracycline, demeclocycline, rolitetracycline, doxycycline, tetracycline and minocycline. Other antibiotics such as chloramphenicol, rifamycin, rifampicin and thiamphenicol.

Chemotherapeutic agents such as the sulfonamides sulfadiazine, sulfamethizol, sulfadimethoxin, sulfamethoxazole, sulfadimidin, sulfamethoxypyridazine, sulfafurazole, sulfaphenazol, sulfalene, sulfisomidin, sulfamerazine, sulfisoxazole and trimethoprim with sulfamethoxazole or sulfametrole.

Urinary tract antiseptics such as methanamine, quinolones (norfloxacin, cinoxacin), nalidixic acid, nitro-compounds (nitrofurantoine, nifurtoinol) and oxolinic acid.

Drug for anaerobic infections such as metronidazole.

Drugs for tuberculosis such as aminosalicyclic acid, isoniazide, cycloserine, rifampicine, ethambutol, tiocarlide, ethionamide and viomycin.

Drugs for leprosy such as amithiozone, rifampicine, clofazimine, sodium sulfoxone and diaminodiphenylsulfone (DDS, dapsone).

Antifungal agents such as amphotericin B, ketoconazole, clotrimazole, miconazole, econazole, natamycin, flucytosine, nystatine and griseofulvin.

Antiviral agents such as aciclovir, idoxuridine, amantidine, methisazone, cytarabine, vidarabine and ganciclovir.

Chemotherapy of amebiasis such as chloroquine, iodoquinol, clioquinol, metronidazole, dehydroemetine, paromomycin, diloxanide, furoatetinidazole and emetine.

Anti-malarial agents such as chloroquine, pyrimethamine, hydroxychloroquine, quinine, mefloquine, sulfadoxine/pyrimethamine, pentamidine, sodium suramin, primaquine, trimethoprim and proguanil.

Anti-helminthiasis agents such as antimony potassium tartrate, niridazole, antimony sodium dimercaptosuccinate, oxamniquine, bephenium, piperazine, dichlorophen, praziquantel, diethylcarbamazine, pyrantel parmoate, hycanthone, pyrivium pamoate, levamisole, stibophen, mebendazole, tetramisole, metrifonate, thiobendazole and niclosamide.

Anti-inflammatory agents such as acetylsalicyclic acid, mefenamic acid, aclofenac, naproxen, azopropanone, niflumic acid, benzydamine, oxyphenbutazone, diclofenac, piroxicam, fenoprofen, pirprofen, flurbiprofen, sodium salicyclate, ibuprofensulindac, indomethacin, tiaprofenic acid, ketoprofen and tolmetin.

Anti-gout agents such as colchicine and allopurinol.

Centrally acting (opoid) analgesics such as alfentanil, methadone, bezitramide, morphine, buprenorfine, nicomorphine, butorfanol, pentazocine, codeine, pethidine, dextromoramide, piritranide, dextropropoxyphene, sufentanil and fentanyl.

Local anesthetics such as articaine, mepivacaine, bupivacaine, prilocaine, etidocaine, procaine, lidocaine and tetracaine.

Drugs for Parkinson's disease such as amantidine, diphenhydramine, apomorphine, ethopropazine, benztropine mesylate, lergotril, biperiden, levodopa, bromocriptine, lisuride, carbidopa, metixen, chlorphenoxamine, orphenadrine, cycrimine, procyclidine, dexetimide and trihexyphenidyl.

Centrally active muscle relaxants such as baclofen, carisoprodol, chlormezanone, chlorzoxazone, cyclobenzaprine, dantrolene, diazepam, febarbamate, mefenoxalone, mephenesin, metoxalone, methocarbamol and tolperisone.

Corticosteroids comprising:

Mineralocorticosteroids such as cortisol, desoxycorticosterone and flurohydrocortisone.

Glucocorticosteroids such as beclomethasone, betamethasone, cortisone, dexamethasone, fluocinolone, fluocinonide, fluocortolone, fluorometholone, fluprednisolone, flurandrenolide, halcinonide, hydrocortisone, medrysone, methylprednisolone, paramethasone, prednisolone, prednisone and triamcinolone (acetonide).

Androgens comprising:

Androgenic steroids used in therapy such as danazole, fluoxymesterone, mesterolone, methyltestosterone, testosterone and salts thereof.

Anabolic steroids used in therapy such as calusterone, nandrolone and salts thereof, dromostanolone, oxandrolone, ethylestrenol, oxymetholone, methandriol, stanozolol methandrostenolone and testolactone.

Antiandrogens such as cyproterone acetate.

Estrogens comprising estrogenic steroids used in therapy such as diethylstilbestrol, estradiol, estriol, ethinylestradiol, mestranol and quinestrol.

Anti-estrogens such as chlorotrianisene, clomiphene, ethamoxytriphetol, nafoxidine and tamoxifen.

Progestins such as allylestrenol, desogestrel, dimethisterone, dydrogesterone, ethinylestrenol, ethisterone, ethynadiol diacetate, etynodiol, hydroxyprogesterone, levonorgestrel, lynestrenol, medroxyprogesterone, megestrol acetate, norethindrone, norethisterone, norethynodrel, norgestrel, and progesterone.

Thyroid drugs comprising:

Thyroid drugs used in therapy such as levothyronine and liothyronine Anti-thyroid drugs used in therapy such as carbimazole, methimazole, methylthiouracil and propylthiouracil.

Apart from bioactive agents which are water soluble, other water-soluble compounds can be incorporated such as anti-oxidants, ions, chelating agents, dyes, imaging compounds.

Preferred therapeutic agents are in the area of cancer (e.g. antitumor) and cardiovascular disease.

Methods of preparing lipophilic drug derivatives which are suitable for nanoparticle or polymersome formulation are known in the art (see e.g., U.S. Pat. No. 5,534,499 describing covalent attachment of therapeutic agents to a fatty acid chain of a phospholipid). Drugs in the present invention can also be prodrugs.

The drug may be present in the inner, the outer, or both of the compartments of the carrier, e.g. in the cavity and/or in the shell of the polymersome. The distribution of the drug is independent of the distribution of any other agents comprised in the drug carrier, such as a paramagnetic chemical shift reagent or a paramagnetic agent. A combination of drugs may be used and any of these drugs may be present in the inner, the outer, or both of the compartments of the drug carrier, e.g. in the cavity and/or in the shell of the polymersome.

Further uses:

As indicated above, the chelating amphiphilic polymers of the invention can be combined with non-chelating amphiphilic polymers.

Also, in the case of polymersomes based in chelating amphiphilic polymers, disease-specific molecular probes can be provided in the polymersome shell, e.g. by having compounds possessing a hydrophobic tail suitable to penetrate into the surface of the polymersome, wherein the other end of the compounds contains a ligand as desired. This allows the polymersomes to be used as contrast agents that can preferentially locate at desired or suspect body sites, which then can be made visible by MRI.

It is to be understood that the invention is not limited to the embodiments and formulae as described hereinbefore. It is also to be understood that in the claims the word "comprising" does not exclude other elements or steps. Where an indefinite or definite article is used when referring to a singular noun e.g. "a" or "an", "the", this includes a plural of that noun unless something else is specifically stated.

The invention will be illustrated with reference to the following, non-limiting Examples and Figures.

BRIEF DESCRIPTION OF THE DRAWINGS

The patent or application file contains at least one drawing executed in color. As the color drawings are being filed electronically via EFS-Web, only one set of the drawings is submitted.

EXAMPLES

Example 1

Synthesis of DOTA-Functionalized poly(ethylene oxide)-block-poly(butadiene) (5)

Figure 1:
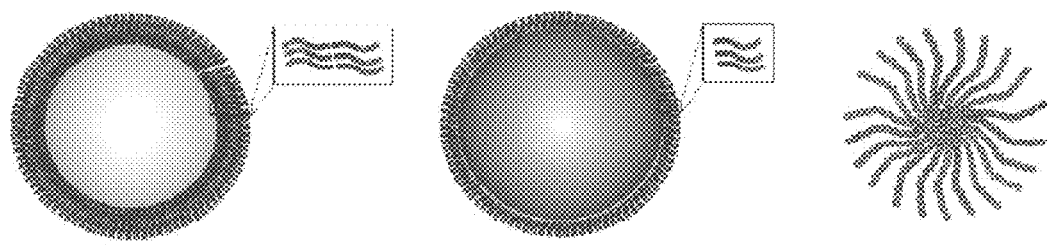
FIG. 1 Self-assembled nanostructures containing amphiphilic copolymers. Polymersomes (left), polymer-stabilized emulsions (middle), and polymeric micelles (right).
Figure 2:
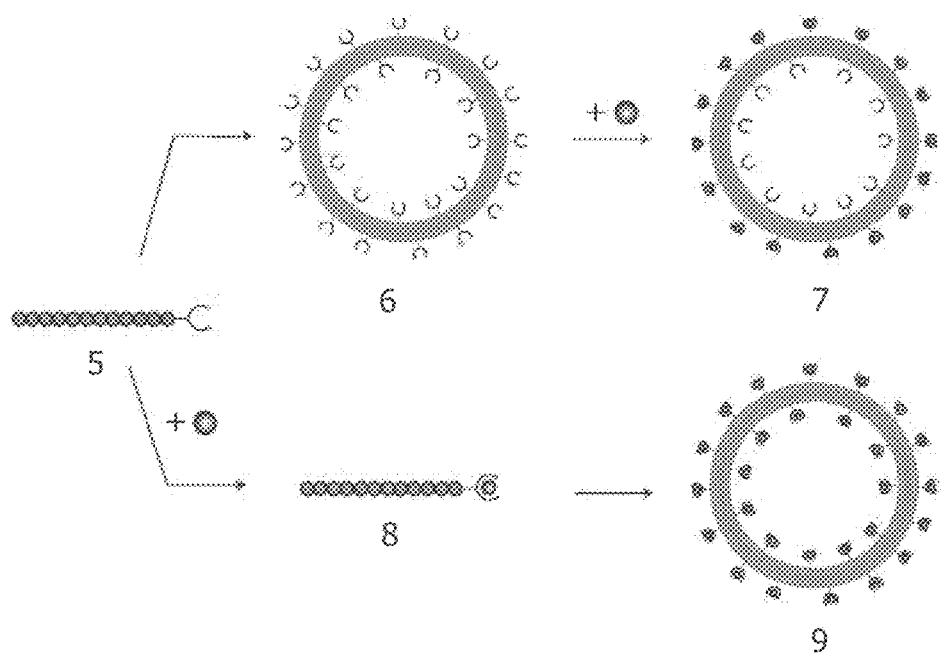
FIG. 2 Schematic representation of Gd(III)DOTA-functionalized polymersomes as $T_{1,2}$-weighted contrast agents for Magnetic Resonance Imaging (MRI).
Figure 3:
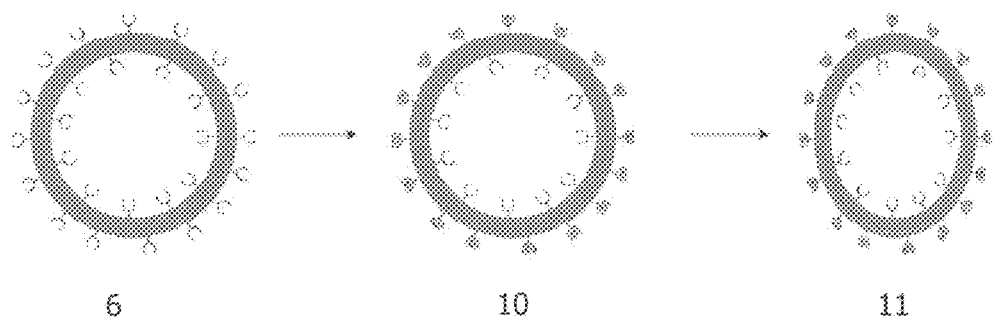
FIG. 3 Schematic representation of DOTA-functionalized polymersomes. Spherical polymersomes containing DOTA-terminated copolymers in the polymer layer (6, left). The reaction of the DOTA-moieties with paramagnetic metals yields spherical polymersomes (10, middle), in which the paramagnetic complexes point outward to the bulk water. Deformation of the polymersomes (10) in response to osmotic pressure affords aspherical polymersomes (11, right).
Figure 4:
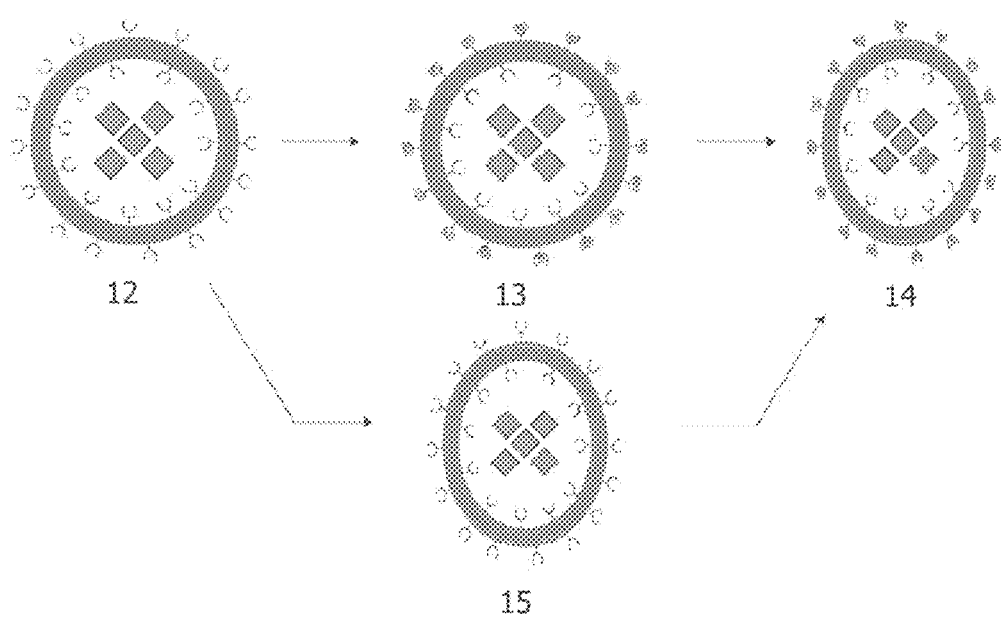
FIG. 4 Schematic representation of DOTA-functionalized polymersomes containing a chemical shift agent in the inner aqueous compartment. Spherical polymersomes containing DOTA-terminated copolymers in the polymer layer (12, top left). The reaction of the DOTA-moieties of 12 with a paramagnetic metal yields spherical polymersomes (13, top middle), in which the paramagnetic complexes point outward to the bulk water. The deformation of 12 in response to osmotic pressure gives aspherical polymersomes (15, bottom). Aspherical polymersomes containing a chemical shift agent in the inside and paramagnetic complexes pointing outward to the bulk water (14, top right) can be obtained from either 13 or 15.
Figure 5:
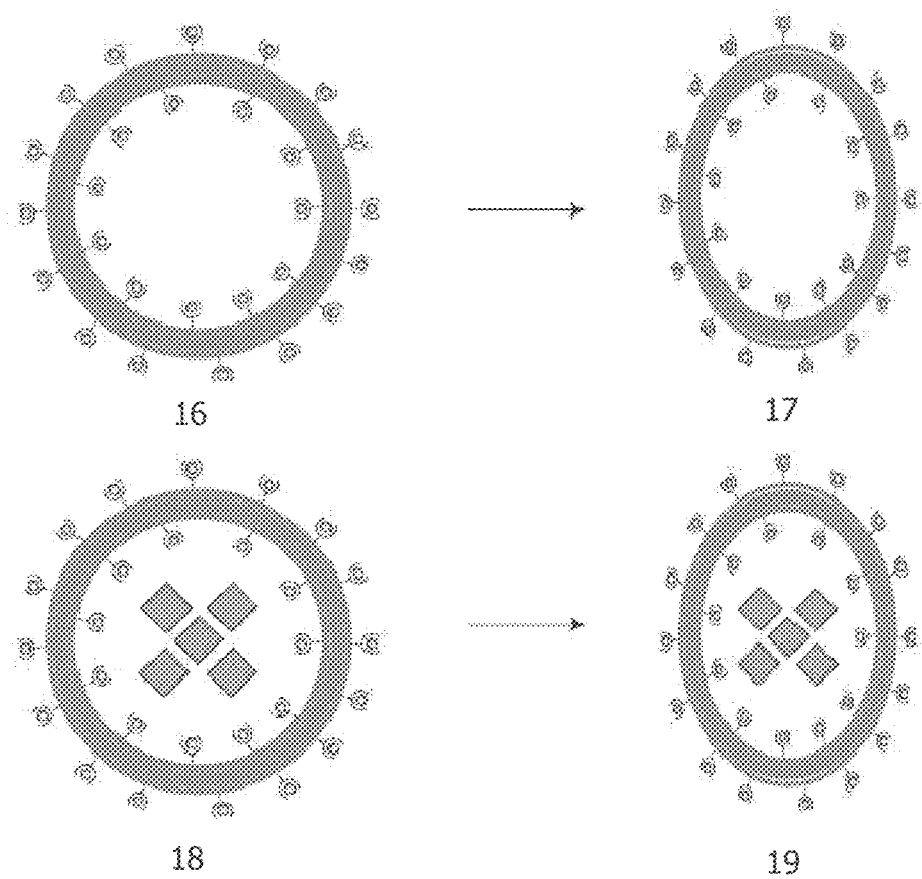
FIG. 5 Schematic representation of polymersomal CEST MRI contrast agents containing paramagnetic complexes of DOTA copolymers on both sides of the polymer layer. Spherical polymersomes (16, top left), aspherical polymersomes (17, top right), spherical polymersomes containing a chemical shift agent in the inner aqueous compartment (18, bottom left), and aspherical polymersomes containing a chemical shift agent in the inner aqueous compartment (19, bottom right).
Figure 6:
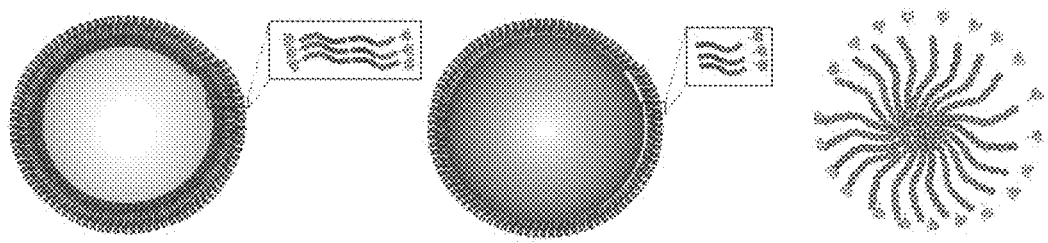
FIG. 6 Polymersomes, polymer-stabilized emulsions, and polymeric micelles for nuclear imaging, showing at the outside of the structure a label e.g. for nuclear imaging.
Figure 7:
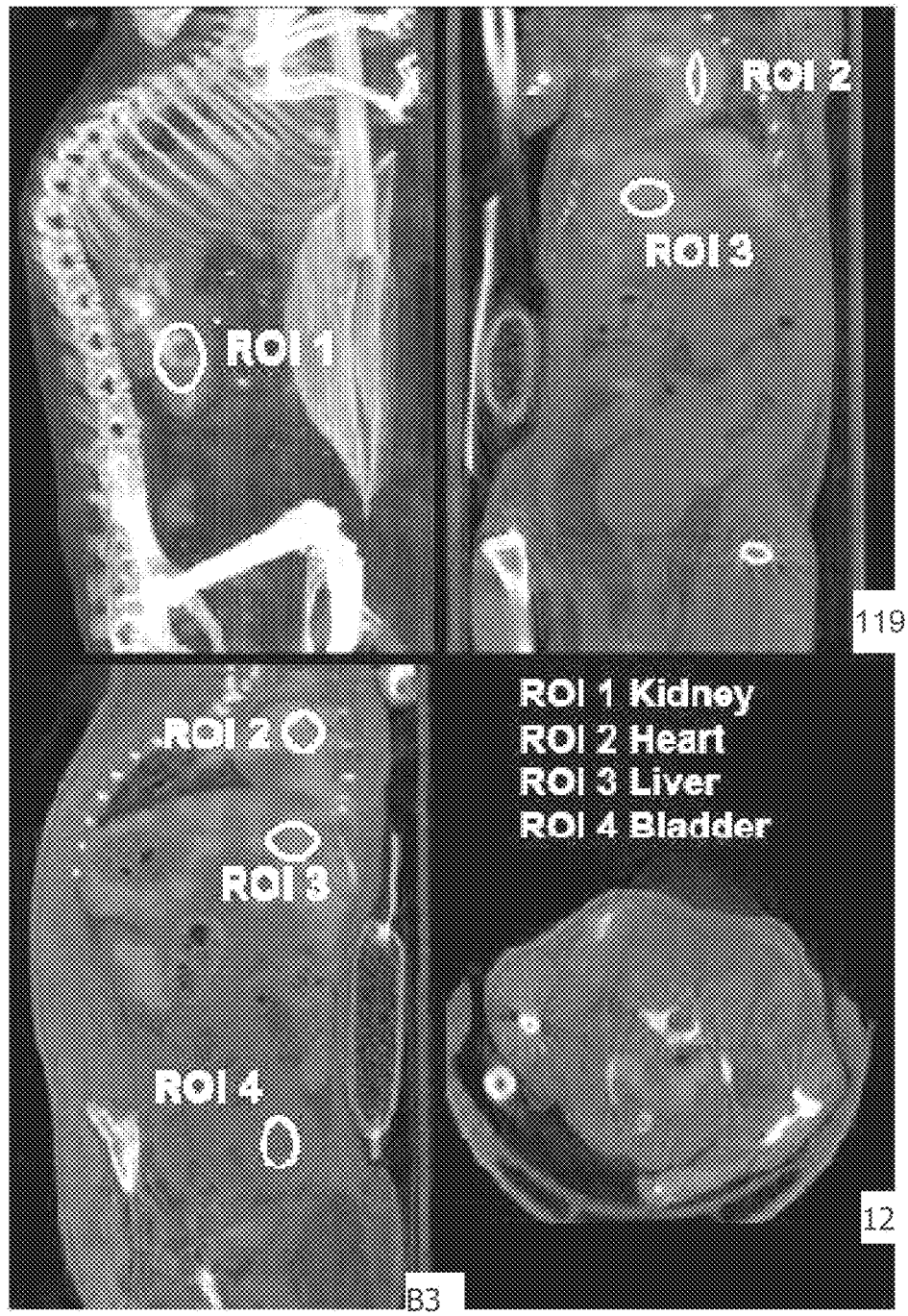
FIG. 7 SPECT/CT image of $^{111}$Indium-labeled emulsion 4 hours post-injection. Maximum intensity projection of CT coregistrated with the SPECT image (top left); coronal SPECT/CT slice visualizing the heart and liver (top right); sagittal SPECT/CT slice visualizing the heart, liver and kidney (bottom left); transversal SPECT/CT slice (bottom right).

PBD(2500)-b-PEO(1300) (1) was dissolved in acetone (18 mL) and the solution was concentrated under reduced pressure in order to remove residual isopropanol. In order to remove traces of water, the copolymer was dissolved in toluene (15 mL) and this solution was concentrated in vacuo. Subsequently, PBD(2500)-b-PEO(1300) (4.90 g, 1.29 mmol) was dissolved in DCM (15 mL) under an atmosphere of nitrogen. The obtained solution was cooled till 0° C. and p-tosylchloride (0.497 g, 2.60 mmol) was added. The mixture was stirred for 30 min at 0° C. and KOH (0.640 g, 11.4 mmol) was added gently. The mixture was stirred overnight at room temperature. The reaction mixture was washed with water (2×30 mL) and brine (2×15 mL). The aqueous layer was extracted with DCM (30 mL) and the combined organic layers were dried over MgSO$_4$, filtered and the solution was concentrated under reduced pressure to yield 2 (62%, 3.2 g, 0.81 mmol). The tosylate-functionalized copolymer (2) (3.2 g, 0.81 mmol) was dissolved in toluene (12 mL) and a solution of 7 N NH$_3$ in MeOH (12 mL, 84 mmol) was added. The reaction was performed at 50° C. for 63 h. Then, the solvent was removed under reduced pressure. The crude mixture was dissolved in DCM (10 mL). The obtained solution was washed with water (2×20 mL), brine (2×10 mL), and saturated NaHCO$_3$ (aq) (10 mL). The aqueous layer was extracted with DCM (40 mL). The combined organic layers were dried over MgSO$_4$. The suspension was filtered and the filtrate was concentrated under reduced pressures to give 3 (1.55 g, 0.41 mmol) in a yield of 50%. The amine-functionalized copolymer (3) (1.2 g, 0.31 mmol) was dissolved in DME (12 mL) and, subsequently, DOTA-based building block (4) (0.347 g, 0.35 mmol) and Et$_3$N (0.9 mL, 6.5 mmol) were added. The mixture was stirred for 26 hrs at room temperature under an atmosphere of nitrogen. The obtained solution was concentrated under reduced pressure. The crude mixture was dissolved in toluene and the solution was concentrated under reduced pressure. The DOTA-functionalized poly(ethylene oxide)-block-poly (butadiene) (5) was obtained in quantitative yield.

Example 2

Self-Assembly of DOTA-Functionalized Copolymers and the Complexation with Gd(III)

Polymer vesicles with an average diameter of 100-150 nm were formed by the thin film hydration technique coupled with sequential extrusions. In brief, the DOTA-functionalized poly(butadiene(1,2-addition)-b-ethylene oxide) ($M_n$(g/mol): PBD(2500)-b-PEO(1300), PD=1.04, and $f_{EO}$=0.34) was dissolved in CHCl$_3$. The solvent was gently removed under reduced pressure and a thin polymer film was obtained. The film was hydrated in 20 mM HEPES solution (pH 7.4). After overnight heating at 50° C. followed by ten freeze-thaw cycles at −177° C. and 70° C., the dispersion was extruded several times through polycarbonate filters with a pore diameter of 1 μm, 0.4 μm, 0.2 μm, and 0.1 μm. Subsequently, a solution of GdCl$_3$ (5 equivalents) in 20 mM HEPES solution at pH 7.4 was added to the polymersome dispersion at 50° C. for 2 hours. Subsequently, the polymersomes were dialyzed overnight to remove the excess of Gd(III). Dialysis was performed against a 20 mM HEPES solution at pH 7.4. The mean average radius of the polymersomes was determined by dynamic light scattering (DLS). The shape of the polymer vesicles was studied by cryo-TEM. The concentration of gadolinium was determined by ICP-MS. The longitudinal and transverse relaxation times ($T_1$ and $T_2$) were determined at 60 MHz.

Example 3

P Aspherical Polymersomes Containing a Chemical Shift Agent and Paramagnetic Complexes of DOTA-Terminated Polymers (14)

Polymer vesicles with an average diameter of 100-150 nm were formed by the thin film hydration technique coupled with sequential extrusions, as described in example 1. In this case the film was hydrated in 20 mM HEPES solution (pH 7.4) containing 65 mM [Tm(hpdo3a)(H$_2$O)]. After overnight heating at 50° C. followed by ten freeze-thaw cycles at −177° C. and 70° C., the dispersion was extruded several times through polycarbonate filters with a pore diameter of 1 μm, 0.4 μm, 0.2 μm, and 0.1 μm. The obtained polymersomes (12) were dialyzed overnight to remove [Tm(hpdo3a)(H$_2$O)] that was not entrapped after hydration of the lipidic film, and to obtain aspherical polymersomes (15). Dialysis was performed with a 20 mM HEPES buffer containing 0.3 M NaCl. Subsequently, a solution of TmCl$_3$ (5 equivalents) in 20 mM HEPES buffer containing 0.3 M NaCl was added to the polymersome dispersion at 50° C. for 2 hours. The polymersomes (14) were dialyzed overnight to remove the excess of Tm. Dialysis was performed against a 20 mM HEPES buffer containing 0.3 M NaCl (pH 7.4). The mean average radius of the polymersomes (14) was determined by dynamic light scattering (DLS). The shape of the polymer vesicles was studied by cryo-TEM. The concentration of gadolinium was determined by ICP-MS. The longitudinal and transverse relaxation times ($T_1$ and $T_2$) were determined at 60 MHz.

Example 4

Radiolabeled Polymersomes and Emulsions
Preparation of the Polymer-Stabilized Emulsion Emulsions were prepared from octan-2-yl 2,3,5-triiodobenzoate (25% weight/volume) using 2% weight/weight of poly(butadiene(1,2 addition)-block-poly(ethylene oxide) ($f_{EO}$ 0.61; $Mw_{phil}$=2033 g/mol; $Mw_{phob}$=1305 g/mol) and 5 mol % of DOTA-functionalized copolymer (5). The emulsions were prepared in a 2.1 mM THAM buffer containing 152 mM NaCl at pH 7.4 using a high pressure microfluidizer system (Microfluidizer M110S, Microfluidics Int. Corp., Newton Mass.) at 70° C. Extensive dialysis was performed against a THAM buffer (1 L) containing Chelex (2 g/L) for three days. Subsequently, the polymer-stabilized emulsions were filtrated through a 450 nm filter.

Radiolabeling of the Emulsions

The emulsion stabilized with the DOTA-copolymer (300 μL) was incubated with 30 MBq of $^{111}$InCl$_3$ in 0.05 M HCl (4 μL)[1] for 1 hour at 70° C. Subsequently, free DTPA was added to the reaction mixture to scavenge free $^{111}$In. 1 μL of the reaction mixture was applied on a silica-coated TLC plate. A solution of 200 mM EDTA containing 9.0 g/L NaCl was used as an eluent. The TLC was analyzed on a FLA-7000 phosphoimager (Fuji Film, Tokyo, Japan) and the radiolabeling was quantified using Aida software (Fuji film). The radiolabeling efficiency was 65% with 30 MBq of $^{111}$InCl$_3$. The radiolabeling on a smaller scale (4.6 MBq of $^{111}$InCl$_3$ in 100 μL emulsion) gave a yield of 97%. Although this yield is higher, 4.6 MBq would not be enough for imaging purposes. Therefore, the described procedure with 30 MBq $^{111}$In was used for in-vivo studies. The radiolabeled emulsions were tested in male Swiss mice (Charles River, Maastricht, the Netherlands) for a dual modality SPECT/CT scan. The radiolabeled emulsion (200 μL) with an activity of 20.5 MBq was injected intravenously. SPECT/CT scans were performed on a NanoSPECT/CT (Bioscan). The animal experiment was approved by the Institutional Ethical Review Committee for animal experiments of the Maastricht University (Maastricht, the Netherlands).

The invention claimed is:

1. A particle comprising:
   a non-chelating amphiphilic polymer; and
   a self-assembled structure, the self-assembled structure comprising a chelating amphiphilic polymer,
      wherein the chelating amphiphilic polymer is capable of self-assembly,
      wherein the chelating amphiphilic polymer comprises a hydrophilic block and a hydrophobic block,
      wherein the hydrophilic block is provided with a chelating moiety,
      wherein the chelating moiety is selected from the group consisting of DOTA, DTPA, HYNIC, and desferoxamine as an end-group wherein the hydrophilic block is a poly (ethylene oxide) block, preferably having a weight-average molecular weight of from 500 to 10,000, wherein the hydrophobic block has a Tg of below 70° C., wherein the hydrophobic block is selected from the group consisting of poly (butadiene), poly (isoprene), and poly (ethylethylene).

2. The particle according to claim 1, wherein the non-chelating amphiphilic polymer comprises a poly (oxy ethylene) chain as a hydrophilic block, wherein the chain is longer than the hydophilic block of the chelating amphiphilic polymer.

3. The particle according to claim 1, further comprising a drug.

4. A CEST MRI contrast agent comprising a particle in accordance with claim 1, wherein the particle is a polymersome,
   wherein the polymersome has a wall formed by a bilayer of one or more amphiphilic polymers,
   wherein the bilayer comprises a chelating amphiphilic polymer,
   wherein the wall encloses a cavity,
   wherein the cavity comprises a pool of proton analytes,
   wherein the proton analytes are capable of diffusion through the wall, wherein chelating moieties of the chelating amphiphilic polymers extending into the direction of the cavity comprise a chelated paramagnetic material.

5. The CEST MRI contrast agent according to claim 4, wherein the CEST MRI contract agent has a non-spherical shape.

6. A SPECT or PET contrast agent comprising a particle in accordance with claim 1,
   Wherein the particle is a polymer-stabilized oil-in-water emulsion,
   Wherein chelating moieties of the chelating amphiphilic polymer are provided with a chelated radionuclide suitable for SPECT or PET.

7. A spectral CT contrast agent comprising a particle in accordance with claim 1, wherein chelating moieties of the chelating amphiphilic polymer are provided with a high-Z material.

8. A method of making a particle, wherein the particle comprises a non-chelating amphiphilic polymer and a self-assembled structure, the self-assembled structure comprising a chelating amphiphilic polymer, wherein the chelating amphiphilic polymer is capable of self-assembly,
   wherein the chelating amphiphilic polymer comprises a hydrophilic block and a hydrophobic block,
   wherein the hydrophilic block is provided with a chelating moiety, wherein the chelating moiety is selected from the group consisting of DOTA, DTPA, HYNIC, and desferoxamine as an end-group,
   wherein one or more of the chelating moieties comprises a metal ion in the form of a coordination complex,
   wherein the metal ions are chelated at the inside, wherein a chelating amphiphilic polymer is subject to an aqueous environment so as to form a bilayer enclosing a cavity, wherein the chelating moieties are subjected to the formation of coordination complexes with metal ions prior to the formation of the bilayer, the method comprising:
   creating the amphiphilic polymer; and
   after creating the amphiphilic polymer coupling the chelating moiety to the hydrophilic block,
   wherein the hydrophilic block is a poly (ethylene oxide) block, preferably having a weight-average molecular weight of from 500 to 10,000,
   wherein the hydrophobic block has a Tg of below 70° C.,
   wherein, the hydrophobic block is selected from the group consisting of poly (butadiene), poly (isoprene), and poly (ethylethylene).

* * * * *